United States Patent [19]

Imanari et al.

[11] Patent Number: 5,225,593
[45] Date of Patent: Jul. 6, 1993

[54] PROCESS FOR PREPARING PYRUVATE

[75] Inventors: Makoto Imanari; Katufumi Kujira; Hiroshi Iwane, all of Ibaraki, Japan

[73] Assignee: Research Association for Utilization of Light Oil, Tokyo, Japan

[21] Appl. No.: 707,946

[22] Filed: May 28, 1991

Related U.S. Application Data

[63] Continuation of Ser. No. 604,376, Oct. 29, 1990, abandoned, which is a continuation of Ser. No. 330,808, Mar. 30, 1989, abandoned.

[30] Foreign Application Priority Data

Apr. 4, 1988 [JP] Japan .................................. 63-82637
Jul. 4, 1988 [JP] Japan ................................ 63-167266

[51] Int. Cl.$^5$ .................... C07C 51/16; C07C 51/235; C07C 51/245
[52] U.S. Cl. .................................................... 562/538
[58] Field of Search ........................................ 562/538

[56] References Cited

FOREIGN PATENT DOCUMENTS 0001070 3/1979 European Pat. Off. .
0008699 3/1980 European Pat. Off. .
0112261 12/1983 European Pat. Off. .
2527600 5/1982 France .

Primary Examiner—José G. Dees
Assistant Examiner—Joseph M. Conrad, III
Attorney, Agent, or Firm—Oblon, Spivak, McClelland, Maier & Neustadt

[57] ABSTRACT

A process for preparing pyruvate in high yield is disclosed, comprising reacting propylene glycol with molecular oxygen in an aqueous solution in the presence of a platinum catalyst containing a metallic component selected from the group consisting of lead, thallium, and cadmium while controlling the pH of the reaction mixture between 7 and 9. The crude pyruvate can be purified by treating with activated carbon in the presence of water.

3 Claims, No Drawings

PROCESS FOR PREPARING PYRUVATE

This application is a continuation of application Ser. No. 07/604,376 filed on Oct. 29, 1990, now abandoned which is a continuation of Abandoned application Ser. No. 07/330,808, filed Mar. 30, 1989.

FIELD OF THE INVENTION

This invention relates to a process for preparing pyruvate. More particularly, it relates to an improved process for preparing pyruvate by reacting propylene glycol with molecular oxygen in the presence of a platinum catalyst.

BACKGROUND OF THE INVENTION

Pyruvic acid is an important intermediate in the in vivo metabolism and a starting material for synthesizing various physiologically active substances. For example, L-tryptophan is obtained by enzymatic reaction of tryptophanase on indole, pyruvic acid, and ammonia.

Conventional processes for preparing pyruvic acid include a process comprising reacting sodium cyanide and acetyl chloride to synthesize acetyl cyanide and hydrolyzing the acetyl cyanide, and a process comprising reacting tartaric acid and potassium hydrogensulfate. These processes not only start with expensive raw materials but attain low yields and have therefore been regarded not advantageous.

It has been proposed to oxidatively dehydrogenate a lactic ester in a gaseous phase to prepare pyruvic acid as disclosed in JP-B-57-24336 and JP-B-56-19854 (the term "JP-B" as used herein means an "examined published Japanese patent application") and JP-A-54-122222 (the term "JP-A" as used herein means an "unexamined published Japanese patent application"). This process also uses expensive lactic acid as a raw material and requires conversion of lactic acid to its ester. In addition, the reaction product is obtained in the form of a pyruvic ester, it should be subjected to hydrolysis to obtain pyruvic acid. Therefore, the process is not always industrially advantageous.

Processes for preparing pyruvic acid by liquid phase oxidation include a process using hydroxyacetone as a starting material as disclosed in JP-A-54-39016, JP-A-54-76524, and JP-A-54-132523, a process starting with lactic ester as disclosed in JP-A-58-62136, and a process starting with lactic acid as disclosed in JP-A-54-138514 and JP-A-55-33418. However, hydroxyacetone is difficult to obtain and expensive. The process using a lactic ester attains low yields and is attended by the safety problem. The process using lactic acid is industrially unsatisfactory because of expensiveness of lactic acid.

JP-B-51-28614 discloses a process in which propylene glycol is contacted with molecular oxygen in an alkaline aqueous solution in the presence of a platinum element as a catalyst as disclosed in JP-B-51-28614. This process, however, chiefly aims at preparation of lactic acid, only obtaining low selectivity to pyruvic acid. Although it is suggested in the publication that reaction be conducted at relatively low temperatures for the synthesis of pyruvic acid, the selectivity to pyruvic acid reached in the working example where the reaction was conducted at 30° C. was only 51%.

JP-A-54-132519 also relates to oxidation of glycol, claiming that a combination of a platinum catalyst and lead shows an increased catalytic activity. The publication describes that oxidation of propylene glycol in the presence of such a catalyst gives lactic acid in high yields, but there is no description about the preparation of pyruvic acid. Although this process employs a relatively low reaction temperature (i.e., 40° to 50° C.), the yield of pyruvic acid was proved low by the inventors' study. The pH of the reaction system is recommended to be maintained at 8 to 11 in the publication, but the inventors also revealed that it is still difficult to obtain pyruvic acid in high yields even with the pH controlled.

On the other hand, nothing is known about purification of pyruvates. There is only found a proposal of using isopropanol in isolation of pyruvates as disclosed in JP-A-55-98132.

A pyruvate is poor in heat stability and, when concentrated, liable to form a dimer even in a low temperature. Also during the reaction, for example, the liquid phase oxidation of propylene glycol, there are produced various impurities, such as an acetate formed by decarboxylation of a pyruvate, a pyruvate dimer, and a lactate as an intermediate. The above-described technique of JP-A-55-98132 fails to substantially remove these impurities.

SUMMARY OF THE INVENTION

One object of this invention is to provide an improvement in a process for preparing pyruvate comprising liquid phase oxidation of inexpensive propylene glycol, which achieves an increased selectivity to pyruvate and an increased yield.

Another object of this invention is to provide a process for preparing high purity pyruvate including removal of impurities in a crude pyruvate.

As a result of extensive investigations, it has now been found that the above objects of this invention can be accomplished by using a catalyst composed of a platinum catalyst which has conventionally been used in liquid phase oxidation of glycol and a specific metallic component, controlling the pH of the reaction mixture, and/or treating the crude pyruvate resulting from liquid phase oxidation of propylene glycol with activated carbon.

That is, the present invention relates to a process for preparing pyruvate which comprises reacting propylene glycol with molecular oxygen in an aqueous solution in the presence of a platinum catalyst, wherein said platinum catalyst contains a metallic component selected from the group consisting of lead, thallium, and cadmium and the pH of the reaction mixture is maintained at 7 to 9.

The present invention further relates to a process for preparing an purifying pyruvate which comprises treating a crude pyruvate obtained by liquid phase oxidation of propylene glycol with activated carbon.

DETAILED DESCRIPTION OF THE INVENTION

The oxidation of propylene glycol is carried out in a liquid phase using propylene glycol in the form of an aqueous solution. The concentration of the propylene glycol aqueous solution usually ranges from 0.5 to 30% by weight and preferably from 1 to 15% by weight. If it is higher than 30%, the resulting pyruvate is apt to be denatured. If it is less than 0.5%, the reaction vessel efficiency is too low for industrial application.

The catalyst which can be used in the present invention comprises platinum having incorporated therein a metallic component selected from the group consisting of lead, thallium, and cadmium. Implicit in the metallic component are metallic elements and metallic compounds.

The catalytic components are usually used as supported on an appropriate carrier. The carrier to be used includes activated carbon, alumina, and magnesia. Commonly employed of them is activated carbon. The amount of platinum to be supported usually ranges from 0.5 to 15% by weight, preferably from 1 to 10% by weight, of the carrier; and the amount of the other element, e.g., lead, to be supported usually ranges from 0.1 to 20% by weight, preferably from 1 to 10% by weight, of the carrier.

The catalyst-on-carrier, e.g., Pt/Pb-on-carbon, can be prepared, for example, by impregnating a mixed aqueous solution of chloroplatinic acid and lead acetate into activated carbon, drying and washing the catalyst, and reducing the catalyst with formalin, hydrazine, or hydrogen as being suspended in water. It can also be prepared by impregnating a commercially available platinum-on-carrier catalyst with a water-soluble lead compound, mostly lead nitrate. A platinum catalyst containing other element than Pb can be prepared similarly.

The amount of the catalyst to be used is not particularly limited. A recommended amount of the total weight of platinum and other element is from 0.5 to 5% by weight based on propylene glycol. The catalyst spent for the reaction can be separated by filtration and reused.

The molecular oxygen to be used for oxidation includes not only pure oxygen but oxygen containing an inert gas (e.g., nitrogen), such as air. The oxygen pressure is usually in the range of from normal pressure to 20 kg/cm$^2$G, preferably from normal pressure to 4 kg/cm$^2$G.

The reaction is usually effected in a neutral to basic region since the reaction rate is very low in an acidic region. In the present invention, the reaction is carried out while controlling the pH in weakly alkaline conditions, concretely between 7 and 9. If the pH of the reaction mixture is higher than 9, the conversion to pyruvate becomes low, and the produced pyruvate undergoes denaturing under such a strongly basic condition to produce by-products, such as a dimer, thus resulting in considerable reduction of the yield of pyruvate.

Maintenance of the reaction mixture at a pH between 7 and 9 can be achieved by successive addition of an aqueous solution of an alkali substance with the progress of the reaction. The alkali substance includes alkali metal hydroxides, e.g., sodium hydroxide, alkali metal carbonates or bicarbonates, alkaline earth metal hydroxides, and ammonium hydroxide.

The reaction temperature ranges from 50° to 80° C. If it is lower than 50° C., the reaction rate becomes low, failing to achieve a high yield of pyruvic acid. If it exceeds 80° C., the produced pyruvic acid undergoes remarkable denaturing to reduce the yield of pyruvic acid. Accordingly, the reaction is carried out at a temperature of from 50° to 80° C. for a period of time as short as possible, usually of from about 2 to about 10 hours.

According to the purification process of the present invention, a crude pyruvate in the form of its aqueous solution in an arbitrary concentration as obtained by the above-described process is treated with activated carbon; or a crude pyruvate in the form of a solid obtained by removing a solvent under reduced pressure is treated with activated carbon in the presence of water. The impurities contained in the crude pyruvate which are supposed to be removed by purification include a pyruvate dimer and a salt of acetic acid, formic acid, lactic acid, etc. The crude pyruvate to be purified may further contain traces of an organic solvent and the starting material, e.g., methanol and propylene glycol.

The activated carbon which can be used in the present invention includes those obtained from coal, coconut shell, charcoal, petroleum pitch, etc. Specific examples of useful commercially available products of activated carbon are "Diahope 008 or S80" and "Diasoap G or W" produced by Mitsubishi Chemical Industries, Ltd.; "HC-30S, GL-30, 2GL, or 4GL" produced by Tsurumi Coal K.K.; "BAC-LP or MP" produced by Kureha Kagaku Kogyo K.K.; "Kuraray Coal GW, GL, GLC, or PK" produced by Kuraray Chemical Co., Ltd.; and "LH2C, W5C, or KL" produced by Takeda Chemical Industries, Ltd.

The conditions for treating the crude pyruvate with activated carbon in the presence of water are not particularly restricted. It is recommended that the treatment be effected by using from about 10 to 1000 cc of activated carbon per gram of the pyruvate at a temperature of 50° C. or lower and at a space velocity (SV) of from 0.1 to 10 hr$^{-1}$ in a column.

The treatment may be carried out under normal pressure, reduced pressure, or under pressure. From considerations for reaction apparatus and operation properties, the treatment is preferably effected at or in the vicinity of normal pressure. The treatment is preferably performed in a flow system. More specifically, the crude pyruvate in the form of an aqueous solution or a dried solid is made to flow through a column packed with activated carbon using water as a solvent at or in the vicinity of normal pressure at room temperature. The effluent aqueous solution can be analyzed by liquid chromatography. Since the impurities in the crude pyruvate, such as a pyruvate dimer and a lactate, are eluted first, the succeeding fraction is collected to obtain an aqueous solution containing a purified pyruvate. The former fraction containing the impurities and a part of the pyruvate can be again passed through the column to recover the pyruvate.

The solvent used here is very cheap water. The spent activated carbon may be regenerated with water for reuse.

The resulting pyruvate aqueous solution can be used as it is, or, if desired, water can be removed by distillation under reduced pressure or reverse osmosis to obtain a concentrate.

The present invention is now illustrated in greater detail by way of the following Examples and Comparative Examples, but it should be understood that the present invention is not deemed to be limited thereto. In these examples, all the percents are by weight unless otherwise indicated.

EXAMPLE 1

Preparation of Pyruvate

In 150 ml of water was dissolved 0.5 g of lead nitrate [Pb(NO$_3$)$_2$], and 6 g of a commercially available 5% platinum-on carbon catalyst (produced by NIPPON ENGELHARD, LTD.) was immersed therein. Water was removed by distillation under reduced pressure to recover 12 g of the catalyst having a water content of 48%.

In a 300 ml-volume flask equipped with a stirrer, a condenser, an inlet for oxygen feed, an inlet for alkali feed, and electrodes for pH measurement were charged 7.6 g (0.1 mol) of propylene glycol, 135.0 g of water, and 5.8 g of the above-prepared lead-added platinum-on-carbon catalyst (water content: 48%). To the flask were fed about 7.2 Nl/hrs of oxygen to effect oxidation at 70° C. for 7 hours while adding dropwise a 10% sodium hydroxide aqueous solution so that sodium hydroxide consumed by the reaction might be always made up to maintain the pH of the reaction mixture between 7 and 9.

The reaction mixture was analyzed by gas chromatography (GC) and high performance liquid chromatography (HPLC). As a result, the conversion of propylene glycol was found to be 92.9% and the reaction mixture was found to contain 8.65 g (78.6%) of sodium pyruvate with slight amounts of a sodium pyruvate dimer and sodium lactate.

EXAMPLE 2

The same procedure of Example 1 was repeated, except for using 5.1 g of a catalyst (water content: 40.0%) prepared by using 0.39 g of thallium (I) nitrate in place of lead nitrate.

The propylene glycol conversion was 90.4%, and the sodium pyruvate yield was 57.6%.

EXAMPLE 3

The same procedure of Example 1 was repeated, except for using 6.3 g of a catalyst (water content: 51.7%) prepared by using 0.82 g of cadmium nitrate [$Cd(NO_3)_2 \cdot 4H_2O$] in place of lead nitrate.

The propylene glycol conversion was 85.2%, and the sodium pyruvate yield was 48.0%.

EXAMPLE 4

The same procedure of Example 1 was repeated, except for using a catalyst recovered from the reaction mixture obtained in Example 1 by filtration.

The propylene glycol conversion and the sodium pyruvate yield were found to be 93.1% and 78.8%, respectively, indicating no deterioration of catalytic activity.

EXAMPLE 5

Purification of Pyruvate

The sodium pyruvate aqueous solution as obtained in Example 1 was distilled under reduced pressure to remove water. The residual solid was found to contain 70% of sodium pyruvate and impurities mainly comprising a sodium pyruvate dimer and sodium lactate.

In a glass column of 35 mm in inner diameter was packed 160 cc of activated carbon "BAC-LP" (a trade name, produced by Kureha Kagaku Kogyo K.K.). After washing the column with a small amount of water, an aqueous solution of 2.0 g of the above separated crude sodium pyruvate (sodium pyruvate content: 1.40 g) was passed through the column from the top end at room temperature. Then, about 400 ml of water was passed through the column at an SV of 0.5 $hr^{-1}$, and the effluent was analyzed by HPLC. There are obtained a sodium pyruvate aqueous solution having a purity of 92.5% as the latter half of the effluent at a recovery of 93.1%.

EXAMPLE 6

Purification of crude sodium pyruvate was carried out in the same manner as in Example 5, except for using 1.0 g of crude sodium pyruvate containing 0.7 g of sodium pyruvate. As a result, a sodium pyruvate aqueous solution having a purity of 99.5% was obtained at a recovery of 64.3%.

EXAMPLE 7

Purification of crude sodium pyruvate was carried out in the same manner as in Example 5, except for using 2.0 g of crude sodium pyruvate (sodium pyruvate content: 1.14 g) which was prepared in the same manner as in Example 1 but with the reaction conditions being varied and using, as activated carbon, "Diahope 008" (a trade name, produced by Mitsubishi Chemical Industries, Ltd.). As a result, a sodium pyruvate aqueous solution having a purity of 98.0% was obtained at a recovery of 40.4%. Thereafter, water was passed through the column to additionally recover a sodium pyruvate aqueous solution having a purity of 99.5%. The total recovery was 56.9%.

COMPARATIVE EXAMPLES 1 TO 3

The same procedure of Example 1 was repeated, except for altering the reaction temperature as shown in Table 1. The reaction results are also shown in Table 1.

TABLE 1

| Comparative Example No. | Reaction Temperature (°C.) | Propylene Glycol Conversion (%) | Sodium Pyruvate Yield (%) |
|---|---|---|---|
| 1 | 15 | 40.0 | 22.0 |
| 2 | 45 | 67.5 | 40.2 |
| 3 | 90 | 93.9 | 38.1 |

COMPARATIVE EXAMPLE 4

The same procedure of Example 1 was repeated, except for using 3.04 g of a commercially available 5% platinum-on-carbon catalyst. The propylene glycol conversion, sodium pyruvate yield, and sodium lactate yield were found to be 81.5%, 14.3%, and 35.8%, respectively.

COMPARATIVE EXAMPLE 5

In the same reaction apparatus as used in Example 1 were charged 7.6 g (0.1 mol) of propylene glycol, 180 g of water, 5.8 g of the same lead-added 5% platinum-on-carbon catalyst as used in Example 1, and 4.0 g (0.1 mol) of sodium hydroxide. The reaction was effected at 70° C. for 7 hours while feeding oxygen at a rate of about 7.2 Nl/hrs. The pH of the reaction mixture was 13.5 at the beginning and 8.45 at the end of the reaction (after 7 hours). The propylene glycol conversion was 95.0%, but the sodium pyruvate yield was only 10.8%.

COMPARATIVE EXAMPLE 6

Two hundred milliliters of an ion exchange resin "SK 1 BS" (a trade name, produced by Japan Water Treatment Service Co.) were packed in a glass column of 35 mm in inner diameter. Through the column were passed 0.45 g of the same crude sodium pyruvate (sodium pyruvate content: 0.26 g) as used in Example 7 and water at an SV of 0.6 $hr^{-1}$. The resulting aqueous solution was proved by HPLC unpurified as having the same composition as charged.

As described above, liquid phase oxidation of propylene glycol in the presence of the conventional platinum catalyst yields lactic acid as a main product, giving only a small proportion of pyruvate. To the contrary, in the present invention, pyruvate can be prepared in high yield by using a specific metallic component-added platinum catalyst and maintaining the pH of the reaction mixture weakly basic. In addition, the reaction condition is mild, and the starting material is cheap.

Further, impurities which are contained in a crude pyruvate as obtained by liquid phase oxidation of propylene glycol and have conventionally been difficult to remove, such as a sodium pyruvate dimer, sodium lactate, etc., can be separated by the purification process of the present invention. Activated carbon used for purification can be repeatedly reused.

Thus, the process for preparing pyruvate according to the present invention, particularly when combined with the purification process of the present invention, is extremely useful for preparing pyruvate useful as a starting material for various physiologically active substances.

While the invention has been described in detail and with reference to specific embodiments thereof, it will be apparent to one skilled in the art that various changes and modifications can be made therein without departing from the spirit and scope thereof.

What is claimed is:
1. A process for preparing pyruvate, which comprises the steps of:
   (i) reacting propylene glycol with molecular oxygen at a temperature of from 50° to 80° C. in an aqueous alkali solution having a pH of from 7 to 9 in the presence of a platinum catalyst which contains a metallic component selected from the group consisting of lead, thallium and cadmium;
   (ii) treating the resulting crude pyruvate containing solution by passing the solution through a flow system of a column containing activated carbon in an amount of from 10 to 1000 cc per gram of the pyruvate in the presence of water and then passing water through the column as a solvent, at a temperature of 50° C. or less and at a space flow velocity of from 0.1 to $10/hr^{-1}$ to elute pyruvate dimer and salts of acetic acid, formic acid and lactic acid in the crude pyruvate first; and then
   (iii) collecting the succeeding fraction of an aqueous solution containing purified pyruvate.

2. A process as claimed in claim 1, wherein said platinum catalyst is supported on activated carbon.

3. A process as claimed in claim 3, wherein said platinum catalyst is composed of from 0.5 to 15% by weight of platinum and from 0.1 to 20% by weight of the metallic component based on the activated carbon.

* * * * *